(12) United States Patent  
Kitamura

(10) Patent No.: US 9,212,115 B2
(45) Date of Patent: Dec. 15, 2015

(54) ALICYCLIC DIOL COMPOUND AND MANUFACTURING METHOD THEREOF

(71) Applicant: Mitsubishi Gas Chemical Company, Inc., Chiyoda-ku (JP)

(72) Inventor: Mitsuharu Kitamura, Kurashiki (JP)

(73) Assignee: Mitsubishi Gas Chemical Company, Inc., Chiyoda-ku (JP)

( * ) Notice: Subject to any disclaimer, the term of this patent is extended or adjusted under 35 U.S.C. 154(b) by 0 days.

(21) Appl. No.: 14/431,907

(22) PCT Filed: Oct. 11, 2013

(86) PCT No.: PCT/JP2013/077710
§ 371 (c)(1),
(2) Date: Mar. 27, 2015

(87) PCT Pub. No.: WO2014/061570
PCT Pub. Date: Apr. 24, 2014

(65) Prior Publication Data
US 2015/0251985 A1    Sep. 10, 2015

(30) Foreign Application Priority Data

Oct. 15, 2012  (JP) ................. 2012-227838

(51) Int. Cl.
*C07C 35/08* (2006.01)
*C07C 35/18* (2006.01)
*C07C 29/16* (2006.01)

(52) U.S. Cl.
CPC ............... *C07C 35/08* (2013.01); *C07C 29/16* (2013.01)

(58) Field of Classification Search
CPC .... C07C 29/141; C07C 45/49; C07C 47/132; C07C 29/149; C07C 29/1285; C07C 29/132; C07C 31/20
USPC .................................................. 568/822, 826
See application file for complete search history.

(56) References Cited

U.S. PATENT DOCUMENTS

| | | | |
|---|---|---|---|
| 2,986,584 A | 5/1961 | Sheers et al. |
| 2002/0042496 A1 | 4/2002 | Teranishi et al. |
| 2011/0040030 A1 | 2/2011 | Mijolovic et al. |
| 2012/0238784 A1 | 9/2012 | Kitamura et al. |
| 2013/0123548 A1 | 5/2013 | Muratore et al. |
| 2013/0345477 A1 | 12/2013 | Kitamura et al. |
| 2014/0087990 A1 | 3/2014 | Kitamura |

FOREIGN PATENT DOCUMENTS

| | | |
|---|---|---|
| JP | 2000 290356 | 10/2000 |
| JP | 2004 124022 | 4/2004 |
| JP | 2005 298555 | 10/2005 |
| JP | 3862538 | 12/2006 |
| JP | 2009 149577 | 7/2009 |
| JP | 2011 521038 | 7/2011 |
| JP | 2012 140354 | 7/2012 |
| WO | 2007 110978 | 10/2007 |
| WO | 2011 002044 | 1/2011 |
| WO | 2011 138747 | 11/2011 |
| WO | 2012 133189 | 10/2012 |

OTHER PUBLICATIONS

International Search Report Issued Dec. 10, 2013 in PCT/JP13/077710 Filed Oct. 11, 2013.

*Primary Examiner* — Jafar Parsa
(74) *Attorney, Agent, or Firm* — Oblon, McClelland, Maier & Neustadt, L.L.P.

(57) ABSTRACT

The alicyclic diol compound of the present invention is represented by the following formula (1).

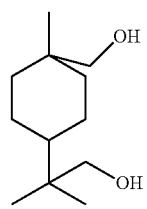

(1)

23 Claims, 6 Drawing Sheets

ALICYCLIC DIOL COMPOUND AND MANUFACTURING METHOD THEREOF

TECHNICAL FIELD

The present invention relates to a new alicyclic diol compound having a cyclohexane ring, and a manufacturing method thereof.

BACKGROUND ART

A polyester resin synthesized from an alicyclic dicarboxylic acid and an alicyclic diol can be applied to use as optical materials, electronic information materials, and medical appliance materials, due to excellence in transparency, heat resistance, weather resistance, gas barrier property, and optical properties.

For example, using 1,4-cyclohexane dicarboxylic acid (1,4-CHDA) as alicyclic dicarboxylic acid, and 1,4-cyclohexane dimethanol (1,4-CHDM) as alicyclic diol, a polyester resin excellent in biodegradability (refer to, for example, Patent Document 1), a conductive polyester emitting a less amount of gas (refer to, for example, Patent Document 2), and a polyester having a short foam-disappearing time, suitable for use in medical application (refer to, for example, Patent Document 3) are synthesized. Furthermore, using tricyclo[3.3.1.1$^{3,7}$]decane dicarboxylic acid as alicyclic dicarboxylic acid, and tricyclo[3.3.1.1$^{3,7}$]decane diol as alicyclic diol, a polyester resin having small optical anisotropy, excellent in moldability, is synthesized (refer to, for example, Patent Document 4).

LIST OF PRIOR ART DOCUMENTS

Patent Document

Patent Document 1
  Japanese Patent Laid-Open No. 2000-290356
Patent Document 2
  Japanese Patent Laid-Open No. 2004-124022
Patent Document 3
  Japanese Patent Laid-Open No. 2005-298555
Patent Document 4
  Japanese Patent No. 3862538

SUMMARY OF INVENTION

Problems to be Solved by Invention

An object of the present invention is to provide a new alicyclic diol compound having a cyclohexane ring and a manufacturing method thereof.

Means for Solving Problems

The present inventor has investigated a method of manufacturing a new alicyclic diol compound represented by the following formula (1) from 4-isopropenyl-1-methyl-1-cyclohexene represented by the following formula (4), and found out that the new alicyclic diol compound represented by the following formula (1) can be manufactured by, for example, reacting 4-isopropenyl-1-methyl-1-cyclohexene represented by the following formula (4) with carbon monoxide in the presence of hydrogen fluoride (hereinafter also referred to as "HF"), subsequently reacting the produced alicyclic dicarboxylic acid fluoride represented by the following formula (3) with alcohol so as to produce an alicyclic dicarboxylic acid ester compound represented by the following formula (2), and then reducing the alicyclic dicarboxylic acid ester compound represented by the following formula (2).

The present invention has been thus accomplished based on the finding.

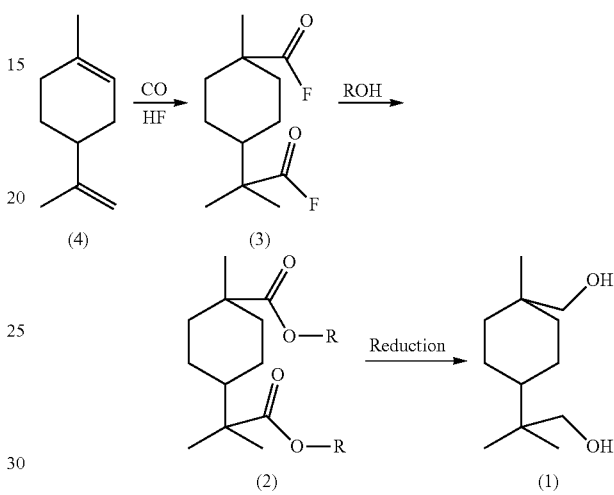

wherein R each independently represent an alkyl group having 1 to 4 carbon atoms.

Specifically, the present invention is described as follows.

[1] An alicyclic diol compound represented by the following formula (1).

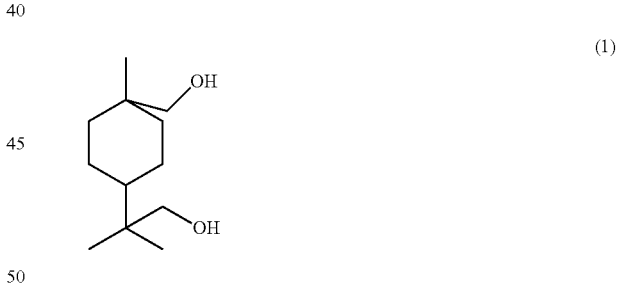

[2] A method of manufacturing an alicyclic diol compound comprising the steps of:

reacting 4-isopropenyl-1-methyl-1-cyclohexene represented by the following formula (4) with carbon monoxide in the presence of hydrogen fluoride so as to produce an alicyclic dicarboxylic acid fluoride represented by the following formula (3);

reacting the produced alicyclic dicarboxylic acid fluoride represented by the following formula (3) with alcohol so as to produce an alicyclic dicarboxylic acid ester compound represented by the following formula (2); and reducing the produced alicyclic dicarboxylic acid ester compound represented by the following formula (2) so as to produce a new alicyclic diol compound represented by the following formula (1):

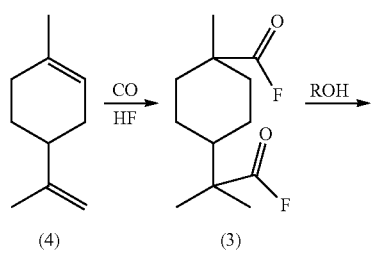

(4) → (3)

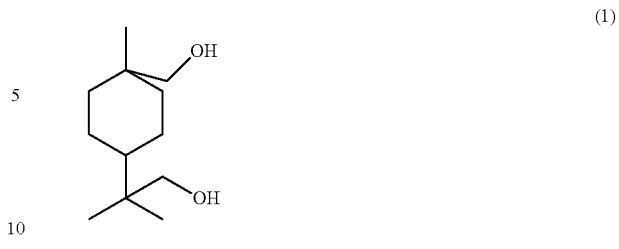

(2) → (1)

wherein R each independently represent an alkyl group having 1 to 4 carbon atoms.

Advantages of Invention

The new alicyclic diol compound represented by the formula (1) of the present invention can be used, for example, as a raw material of polyester resins. Since the manufacturing method of the present invention uses a compound represented by the formula (4) derived from biomass as a raw material, it can be said that the manufacturing method is environment-friendly in terms of carbon neutrality.

MODE FOR CARRYING OUT INVENTION

Figure 1:
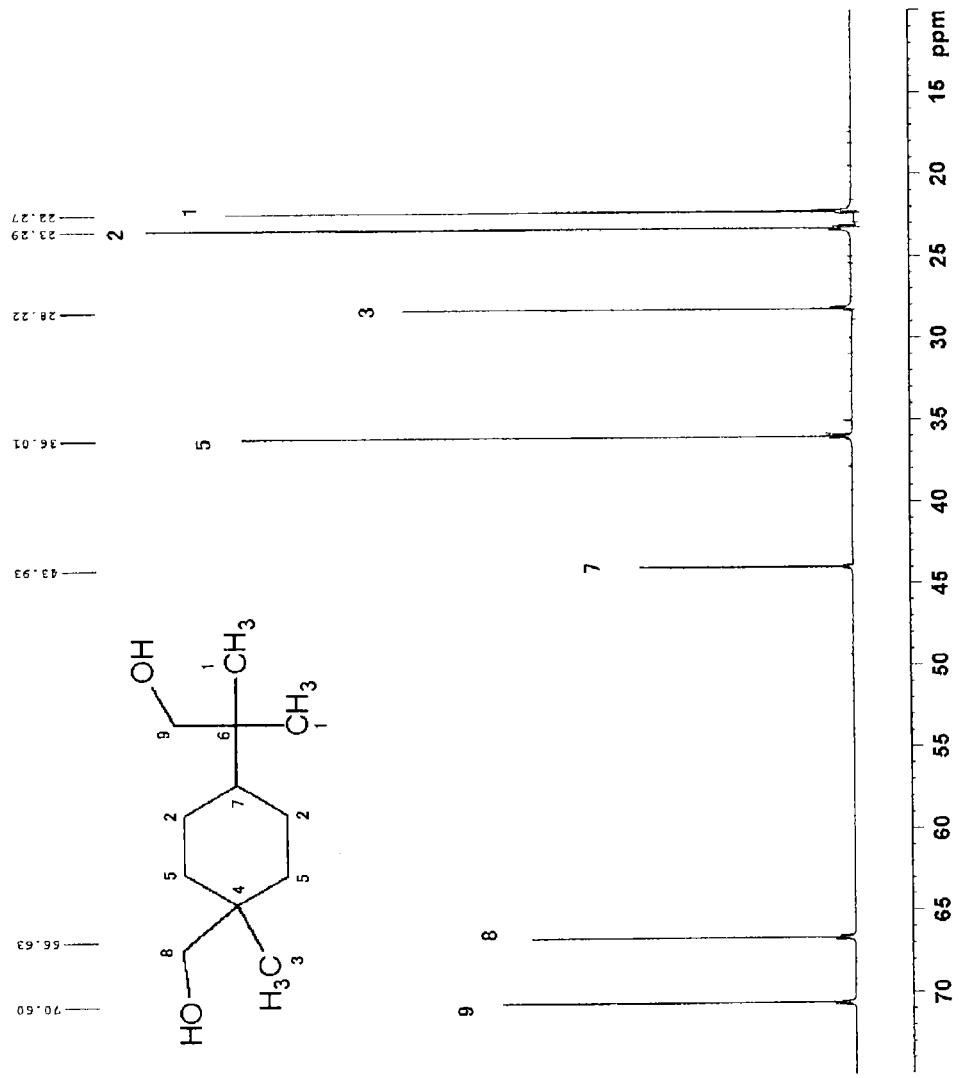
FIG. 1 is a chart showing DEPT 45°-NMR measurement results of a product obtained in Example 1.

The embodiments of the present invention (hereinafter also referred to as "the present embodiment") are described in detail in the following. The following embodiments are, however, provided to illustrate the present invention, and the present invention is not limited thereto only.

The new alicyclic diol compound of the present embodiment is a compound represented by the following formula (1).

(1)

The alicyclic diol compound represented by the formula (1) may be used, for example, as a raw material for polyester resins, and a material excellent in optical properties and heat resistance can be manufactured by using the alicyclic diol compound. Examples of the application of the material having such properties include, but not particularly limited to, optical materials such as lenses.

The method of manufacturing the new alicyclic diol compound of the present embodiment comprises the following steps (a) to (c):

(a) A step of reacting 4-isopropenyl-1-methyl-1-cyclohexene represented by the following formula (4) with carbon monoxide in the presence of hydrogen fluoride (hereinafter also referred to as "HF") so as to produce an alicyclic dicarboxylic acid fluoride represented by the following formula (3)(hereinafter sometimes abbreviated as "carbonylation step");

(b) A step of reacting the produced alicyclic dicarboxylic acid fluoride represented by the following formula (3) with alcohol so as to produce an alicyclic dicarboxylic acid ester compound represented by the following formula (2) (hereinafter sometimes abbreviated as "esterification step"); and (c) A step of reducing the produced alicyclic dicarboxylic acid ester compound represented by the following formula (2) so as to produce an alicyclic diol compound represented by the following formula (1) (hereinafter sometimes abbreviated as "reduction step").

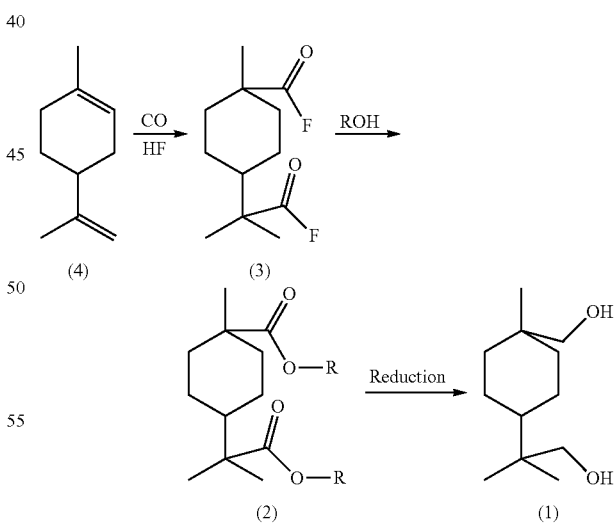

wherein R each independently represent an alkyl group having 1 to 4 carbon atoms.

<(a) Carbonylation Step>

In the step (a), the carbonylation reaction of 4-isopropenyl-1-methyl-1-cyclohexene represented by the following formula (4) is preferably performed in the presence of HF under pressure of carbon monoxide. Through the step (a), an alicyclic carbonyl compound represented by the following formula (3) (hereinafter also referred to as "alicyclic dicarboxylic acid fluoride") is produced. The product of the carbonylation reaction in the step (a) may contain various by-products (containing other isomers).

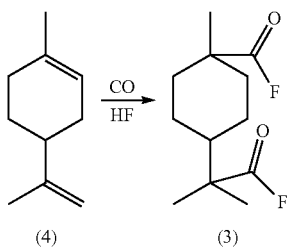

[Carbon Monoxide]

The carbon monoxide for use in the carbonylation step may contain an inert gas such as nitrogen and methane. The carbonylation step is performed under a carbon monoxide partial pressure in the range of preferably 0.5 to 5 MPa, more preferably 1 to 4 MPa, furthermore preferably 1.5 to 3 MPa. Under a carbon monoxide partial pressure of more than 0.5 MPa, the carbonylation reaction proceeds sufficiently without concurrence of side reactions such as disproportionation and polymerization, so that the target substance, i.e. alicyclic dicarboxylic acid fluoride, can be obtained at a high yield. A carbon monoxide partial pressure of 5 MPa or less is preferred, considering the load on equipment.

[Hydrogen Fluoride]

Since HF for use in the carbonylation step functions as a solvent, a catalyst, and a secondary raw material for the reaction, use of substantially anhydrous HF is preferred. In the present embodiment, the substantially anhydrous HF means HF with a water concentration of 200 ppm or less. In the carbonylation step, the amount of HF for use is preferably 4 to 30 times by mole, more preferably 7 to 20 times by mole, furthermore preferably 10 to 15 times by mole, as large as the amount of raw material 4-isopropenyl-1-methyl-1-cyclohexene. With an amount of HF for use of 4 times by mole or more, the carbonylation reaction proceeds efficiently, with concurrence of side reactions such as disproportionation and polymerization being suppressed, so that the target substance, i.e. alicyclic dicarboxylic acid fluoride, can be obtained at a high yield. The amount of HF for use is preferably 30 times by mole or less, more preferably 15 times by mole or less, considering raw material costs and productivity.

[Reaction Conditions]

The type of carbonylation reaction in the step (a) is not particularly limited. Any of a batch type, a semi-continuous type, a continuous type, and the like may be employed.

The reaction temperature of carbonylation reaction in the step (a) is preferably in the range of −50° C. to 30° C., more preferably −40° C. to 0° C., furthermore preferably −30 to −10° C. At a reaction temperature of the carbonylation reaction of 30° C. or less, in particular −10° C. or less, improved selectivity tends to be achieved. The carbonylation reaction in the step (a) is preferably performed at −50° C. or more, considering the reaction rate.

The reaction pressure of carbonylation reaction in the step (a) is preferably in the range of 0.6 to 5.0 MPa, more preferably 1.1 to 4.0 MPa, furthermore preferably 1.6 to 3.0 MPa.

<(b) Esterification Step>

The esterification step is a step of reacting the alicyclic dicarboxylic acid fluoride produced in the carbonylation step with an alcohol having 1 to 4 carbon atoms so as to produce an alicyclic dicarboxylic acid ester compound. In the esterification step, the reaction liquid produced in the carbonylation step may be directly used. Considering the corrosivity of a reaction apparatus, in the esterification step, a method in which a predetermined amount of alcohol is added to the reaction liquid produced in the carbonylation step is preferred. Alternatively, an excessive amount of HF may be distilled away from the reaction liquid produced in the carbonylation step and then alcohol may be added to the reaction liquid for esterification.

Instead of using the reaction liquid of acid fluoride produced in the carbonylation reaction in the esterification step: (I) after distilling excessive amount of HF away, the reaction liquid may be refined by a conventional method such as distillation, so that the acid fluoride can be directly used as a raw material in the subsequent reduction step; or (II) after distilling excessive amount of HF away, the reaction liquid may be hydrolyzed to produce a corresponding carboxylic acid, which is refined by a conventional method such as distillation, so that the carboxylic acid can be used as a raw material in the subsequent reduction step.

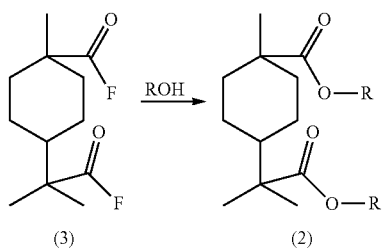

wherein R each independently represent an alkyl group having 1 to 4 carbon atoms.

Specific examples of the alcohol for use in the esterification step include methanol, ethanol, n-propanol, isopropanol, n-butyl alcohol, isobutyl alcohol, and tert-butyl alcohol, though not being particularly limited. Among them, methanol or ethanol is preferred, considering the reactivity. In the esterification step, one type of alcohol may be used alone or two or more types may be used in combination.

The amount of alcohol for use in the esterification step is preferably 1.0 to 2.5 times by mole, more preferably 1.2 to 2.3 times by mole, furthermore preferably 1.5 to 2.0 times by mole, as large as the amount of raw material 4-isopropenyl-1-methyl-1-cyclohexene in the carbonylation step. With an amount of alcohol for use of 1.0 times by mole or more, the remaining amount of unreacted alicyclic dicarboxylic acid fluoride is small, resulting in little corrosion of apparatus in a subsequent step, which is preferable. An amount of alcohol for use of 2.5 times by mole or less is preferred, from the viewpoint of suppressing the corrosion of apparatus by water produced in an intermolecular dehydration reaction of alcohol.

The reaction temperature in the esterification step is preferably −40° C. or more and 20° C. or less, more preferably −30° C. to 10° C., furthermore preferably −30° C. to 0° C., from the viewpoint of suppressing decomposition of the alicyclic dicarboxylic acid ester compound represented by the above formula (2). With a reaction temperature of −40° C. or more, the esterification rate can be accelerated to improve the yield. With a reaction temperature of 20° C. or less, the decomposition of ester can be suppressed and by-product water due to dehydration reaction of alcohol can be suppressed.

The esterification step is preferably performed under normal pressure.

<(c) Reduction Step>

In the step (c), the method for reducing the alicyclic dicarboxylic acid ester compound represented by the formula (2) (hereinafter also referred to as "alicyclic dicarboxylic acid ester compound") produced in the esterification step may be any of the conventional method for reducing a carbonyl compound to alcohol, without particular limitations. The reduction method for use may be, for example, any of hydride reduction, reduction using a metal and a metal salt, and reduction by catalytic hydrogenation, which are described in The Fifth Series of Experimental Chemistry Vol. 14 (Maruzen) pp. 11-27. Among them, reduction by catalytic hydrogenation is preferred from the viewpoint of economic efficiency.

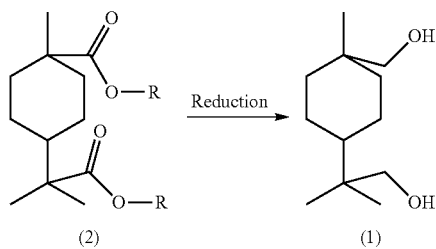

wherein R each independently represent an alkyl group having 1 to 4 carbon atoms.

[Catalytic Hydrogenation Catalyst]

Although the catalyst for use in catalytic hydrogenation of an alicyclic dicarboxylic acid ester compound (hereinafter also referred to as "catalytic hydrogenation catalyst") is not particularly limited as long as being a conventional catalysts for use in hydrogenation of a carbonyl compound, preferably the catalyst includes at least one selected from metals in groups 8 to 11 of the periodic table.

Specific examples of the catalytic hydrogenation catalyst include a catalytic hydrogenation catalyst which contains at least one selected from iron, cobalt, nickel, copper, ruthenium, rhodium, palladium, silver, osmium, iridium, platinum, and gold, though not being particularly limited.

Although the catalytic hydrogenation catalyst may be a solid catalyst or a homogeneous catalyst, a solid catalyst is preferred considering the isolation from reaction products. Examples of the solid catalyst include an unsupported metal catalyst and a supported metal catalyst, though not being particularly limited.

Preferred examples of the unsupported metal catalyst include a Raney catalyst such as Raney nickel, Raney cobalt, and Raney copper, an oxide of platinum, palladium, rhodium, ruthenium, or the like, and a colloidal catalyst.

Examples of the supported metal catalyst include a supported metal catalyst composed of at least one of iron, cobalt, nickel, copper, ruthenium, rhodium, palladium, silver, osmium, iridium, platinum, and gold supported on or blended with a carrier such as magnesia, zirconia, ceria, diatomaceous earth, activated carbon, alumina, silica, zeolite, or titania, though not being particularly limited. Among them, a supported copper catalyst such as a copper-chromium catalyst (Adkins catalyst), a copper-zinc or copper-iron catalyst, a supported platinum catalyst such as Pt/C and Pt/alumina, a supported palladium catalyst such as Pd/C and Pd/alumina, a supported ruthenium catalyst such as Ru/C and Ru/alumina, or a supported rhodium catalyst such as Rh/C and Rh/alumina is preferred. Among these, a catalyst which contains at least one selected from the group consisting of nickel and copper is more preferred in terms of the reaction activity.

In the reduction step, the amount of catalytic hydrogenation catalyst for use is preferably 1 to 100 parts by mass, more preferably 3 to 30 parts by mass, furthermore preferably 5 to 20 parts by mass, relative to 100 parts by mass of the raw material alicyclic dicarboxylic acid ester compound, though depending on the type of catalyst.

[Solvent]

The reduction step can be performed without solvent. Alternatively, a solvent may be used in the step.

Examples of the solvent for use in the reduction step include water; organic acids such as formic acid and acetic acid; aromatic compounds such as benzene, o-dichlorobenzene, toluene, and xylene; hydrocarbons such as hexane, heptane, and cyclohexane; alcohols such as methanol, ethanol, isopropyl alcohol, t-butyl alcohol, ethylene glycol and diethylene glycol; ethers such as dioxane, tetrahydrofuran, dimethoxyethane, and diglyme; or a mixture thereof; though not being particularly limited. Among them, solvent-free; aromatic compounds such as benzene, o-dichlorobenzene, toluene, and xylene; hydrocarbons such as hexane, heptane, and cyclohexane; alcohols such as methanol, ethanol, isopropyl alcohol, t-butyl alcohol, ethylene glycol, and diethylene glycol; ethers such as dioxane, tetrahydrofuran, dimethoxyethane, and diglyme; or a mixture thereof, is preferably employed.

In the reduction step, the amount of solvent for use is preferably 0 to 30 times by mass, more preferably 0 to 20 times by mass, furthermore preferably 0 to 10 times by mass, as large as the amount of alicyclic dicarboxylic acid ester compound represented by the formula (2) produced in the esterification step.

[Reaction Conditions]

A higher hydrogen pressure in the reduction step is more preferred for shifting the reaction equilibrium to the alcohol side. The pressure is preferably 1 to 30 MPa, more preferably 5 to 25 MPa, furthermore preferably 10 to 20 MPa, considering equipment cost.

The reaction temperature in the reduction step is preferably 100° C. or more, more preferably 150° C. or more, furthermore preferably 180° C. or more, from the viewpoint of obtaining a sufficient reaction rate. The reaction temperature in the reduction step is preferably 300° C. or less, more preferably 290° C. or less, furthermore preferably 280° C. or less, from the viewpoint of suppressing the transesterification reaction between an alicyclic diol compound represented by the formula (1) to be produced and an alicyclic dicarboxylic acid ester compound represented by the formula (2).

The reaction pressure in the reduction step is in the range of preferably 1.5 to 30 MPa, more preferably 6 to 25 MPa, furthermore preferably 10 to 20 MPa.

The type of reduction step is not particularly limited. For example, in the case of reduction by catalytic hydrogenation, the type of reduction step is not particularly limited as long as the catalytic hydrogenation reaction is feasible, so that a known, commonly used type may be employed. Examples of the reactor in which the reduction step is performed include a suspended bed reactor for performing catalytic hydrogenation reaction with catalysts fluidized in a fluid, and a fixed bed reactor filled with catalysts to be fixed for performing catalytic hydrogenation reaction by supplying a fluid, though not being particularly limited.

In the reduction step, alcohols having 1 to 4 carbon atoms may be by-produced during the reaction in some cases. The reduction step may be performed with the by-products remaining, or may be performed with the by-products being continuously or intermittently removed during the reaction.

<Other Steps>

The manufacturing method of the present embodiment may comprise other steps other than the steps (a) and (b) described above. Examples of the other step include a liquid-liquid extraction step, a catalyst recovery step, a neutralization and washing step, an auxiliary agent recovery step, and a refining step, though not being particularly limited.

Examples of the refining step include: a step of, after distilling HF away from the reaction liquid containing an alicyclic dicarboxylic acid ester compound represented by the formula (2) produced in the esterification step, refining the reaction liquid by a conventional method such as distillation; and a step of, after separating the hydrogenation catalyst from the products containing the alicyclic diol compound represented by the formula (1) produced in the reduction step, refining the products by a conventional method such as distillation and recrystallization; though not being particularly limited. Through such a refining step, a new high-purity alicyclic diol represented by the formula (1) can be obtained.

EXAMPLES

Hereinafter, the present invention will be specifically described with reference to Examples, but the present invention is not intended to be limited to these examples. Unless otherwise specified, "%" in the following means mass %.

<Analytical Method and Conditions>

[Analysis Conditions for Gas Chromatography]

In gas chromatography, a measurement apparatus GC-17A made by SHIMADZU CORPORATION and a capillary column HR-1 made by ULBON (0.32 mmϕ×25 m×0.50 μm) were used. The temperature-rising conditions were set such that the temperature was raised from 100° C. to 300° C. at a rate of 5° C./min.

[Yield and Isomer Ratio of Dicarboxylic Acid Ester Compound]

By gas chromatography analysis, the area ratios (GC %) of several types of isomeric dicarboxylic acid ester compounds as products were obtained, and the yield and the isomer ratio of the dicarboxylic acid ester compounds were calculated by an internal reference method using the following expression.

{Yield of dicarboxylic acid ester compound(mol %)}={Total acquisition mass of dicarboxylic acid ester compound/256.3}/{Raw material feed mass/136.2}×100

{Isomer ratio(%)}={Methyl-4-(1-methoxy-2-methyl-1-oxopropan-2-yl)-1-methylcyclohexane carboxylate (GC %)}/{Total of dicarboxylic acid ester compounds(GC %)}×100

The isomer in the description means a structural isomer having a carbonyl group at a different insertion position.

[Yield of Alicyclic Diol Compounds]

By gas chromatography analysis, the area ratios (GC %) of several types of isomeric diol compounds as products were obtained, and the yield of 2-(4-(hydroxymethyl)-4-methylcyclohexyl)-2-methylpropan-1-ol was calculated by an internal reference method.

[GC-MS]

As GC-MS measurement apparatus, a GC-MS spectrometer POLARIS Q made by Thermo ELECTRON Corporation was used.

[NMR]

NMR was measured under the following conditions.
Apparatus: Bruker Avance 60011 (600 MHz-NMR)
Mode: Proton, Carbon, DEPT 45°, 90°, and 135°, Carbon i.g., and INADEQUATE
Solvent: CDCl3 (deuterated chloroform)
Internal reference substance: tetramethylsilane Example 1

Manufacturing of methyl-4-(1-methoxy-2-methyl-1-oxopropan-2-yl)-1-methylcyclohexane carboxylate ((a) Carbonylation Step and (b) Esterification Step)

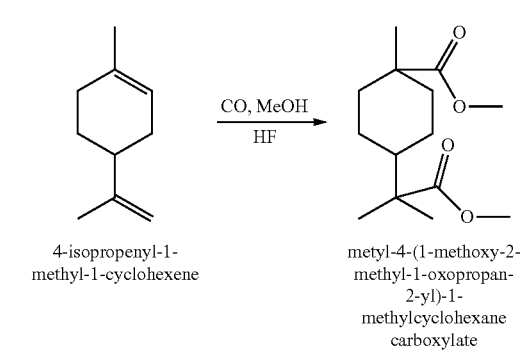

4-isopropenyl-1-methyl-1-cyclohexene metyl-4-(1-methoxy-2-methyl-1-oxopropan-2-yl)-1-methylcyclohexane carboxylate

[Carbonylation Step]

Using a stainless steel autoclave with an internal volume of 500 ml including a Nack drive type stirrer and three inlet nozzles at the top and one extraction nozzle at the bottom, with a jacket for internal temperature control, the carbonylation step was performed as follows.

First, the atmosphere in the autoclave was substituted with carbon monoxide. Subsequently, 230 g (11.5 mol) of anhydrous hydrogen fluoride was introduced into the autoclave, and the liquid temperature in the autoclave was set to −27° C. The inside of the autoclave was then pressurized to 2 MPa with carbon monoxide.

In the autoclave with the reaction temperature being kept at −27° C., and the reaction pressure being kept at 2 MPa, 104.4 g (0.77 mol) of 4-isopropenyl-1-methyl-1-cyclohexene was supplied from the top of the autoclave, so that the carbonylation reaction was performed. After completion of the supply, with stirring of the reaction liquid being continued for about 10 minutes until no absorption of carbon monoxide was observed, an alicyclic dicarboxylic acid fluoride was thereby obtained.

[Esterification Step]

Subsequently, in the autoclave with the reaction temperature being kept at −27° C., 49.1 g (1.53 mol) of methanol was supplied from the top of the autoclave, so that esterification of the alicyclic dicarboxylic acid fluoride was performed with the reaction liquid being stirred for 1 hour.

The reaction liquid was extracted from the bottom of the autoclave into ice water, so that an oil phase and an aqueous phase were separated. Subsequently, the oil phase was washed twice with 100 ml of 2% caustic soda aqueous solution and twice with 100 ml of distilled water, and was dehydrated with 10 g of anhydrous sodium sulfate. After dehydration, the produced liquid was analyzed by gas chromatography. As a result, the yield of the dicarboxylic acid ester compound was 26.6 mol % (on 4-isopropenyl-1-methyl-1-cyclohexene basis), and the yield of methyl-4-(1-methoxy- 2-methyl-1-oxopropan-2-yl)-1-methylcyclohexane carboxylate was 21.1 mol % (on 4-isopropenyl-1-methyl-1-cyclohexene basis, isomer ratio: 79.2%).

[Isolation and Refining of Esterification Reaction Product]

By reduced-pressure distillation of the liquid produced in the esterification step with an evaporator, low-boiling point substances were removed from the liquid. Subsequently, the low-boiling point substance-removed liquid was rectified using a rectification column with a theoretical plate number of 20 (distillation temperature: 177° C., degree of vacuum: 20 torr). Through the rectification, 42.0 g of a product as main fraction having an isomer ratio of 92.0% by gas chromatography analysis (distilled yield: 93.2 mol %, on methyl-4-(1-methoxy-2-methyl-1-oxopropan-2-yl)-1-methylcyclohexane carboxylate basis) was obtained.

[Reduction Step]

Manufacturing of 2-(4-(hydroxymethyl)-4-methylcyclohexyl)-2-methylpropan-1-ol

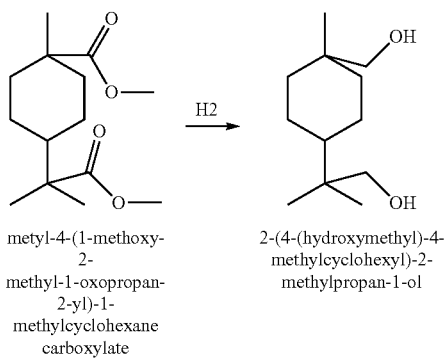

metyl-4-(1-methoxy-2-methyl-1-oxopropan-2-yl)-1-methylcyclohexane carboxylate 2-(4-(hydroxymethyl)-4-methylcyclohexyl)-2-methylpropan-1-ol In an stainless steel autoclave, 3.0 g of a copper-zinc catalyst supported on alumina (made by JGC Catalysts and Chemicals Ltd.) and 30.0 g of the product produced as main fraction in the isolation and refining (containing methyl-4-(1-methoxy-2-methyl-1-oxopropan-2-yl)-1-methylcyclohexane carboxylate with an isomer ratio of 92.0% and other isomers in an amount of 8.0%) were placed, and the mixture was stirred for 15 hours at 280° C., under a hydrogen pressure of 15 MPa, in a solvent-free state with hydrogen passing. The reduction reaction of methyl-4-(1-methoxy-2-methyl-1-oxopropan-2-yl)-1-methylcyclohexane carboxylate was thus performed.

The catalyst was removed by filtering the reaction liquid, so that 19.1 g of a product (mixture) was manufactured, containing 0.8% of methyl-4-(1-methoxy-2-methyl-1-oxopropan-2-yl)-1-methylcyclohexane carboxylate, 9.6% of perhydrogenated product, 89.0% of 2-(4-(hydroxymethyl)-4-methylcyclohexyl)-2-methylpropan-1-ol, and 0.6% of other isomers. The yield of 2-(4-(hydroxymethyl)-4-methylcyclohexyl)-2-methylpropan-1-ol was 78.9 mol % (on methyl-4-(1-methoxy-2-methyl-1-oxopropan-2-yl)-1-methylcyclohexane carboxylate basis).

[Recrystallization Refining of Reduction Reaction Product]

The product obtained in the reduction step was dissolved in methanol. Subsequently, 40 g of n-hexane was slowly poured into the produced solution, and the precipitated crystals were separated by filtration. The obtained product was a white solid with a purity of 100% (12.6 g, crystallization yield: 65.7 mol %, on 2-(4-(hydroxymethyl)-4-methylcyclohexyl)-2-methylpropan-1-ol basis).

<Product Identification>

As a result of GC-MS analysis, the product obtained in the recrystallization refining in Example 1 had a molecular weight of 200.

Using the NMR apparatus, 1H-NMR measurement, 13C-NMR measurement, DEPT 45°, 90°, and 135°-NMR measurement, Carbon i.g.-NMR measurement, and INADEQUATE-NMR measurement were performed. The results of 1H-NMR measurement and 13C-NMR measurement are shown as follows, and the results of DEPT 45°, 90°, and 135°-NMR measurement, Carbon i.g.-NMR measurement, and INADEQUATE-NMR measurement are shown in FIG. 1 to FIG. 6.

[NMR Measurement Results of Product Obtained in Example 1]

1H-NMR (600 MHz, CDCl3, TMS, ppm) δ: 0.700-0.955 (m, 9H), 1.113-1.231 (m, 6H), 1.473-1.560 (m, 2H), 1.638-1.726 (m, 2H), 3.281-3.457 (m, 4H), 4.907 (m, 1H)

13C-NMR (600 MHz, CDCl3, TMS, ppm) δ: 22.27, 23.29, 28.22, 35.07, 36.02, 37.86, 43.94, 49.01, 66.64, 70.60

Figure 2:
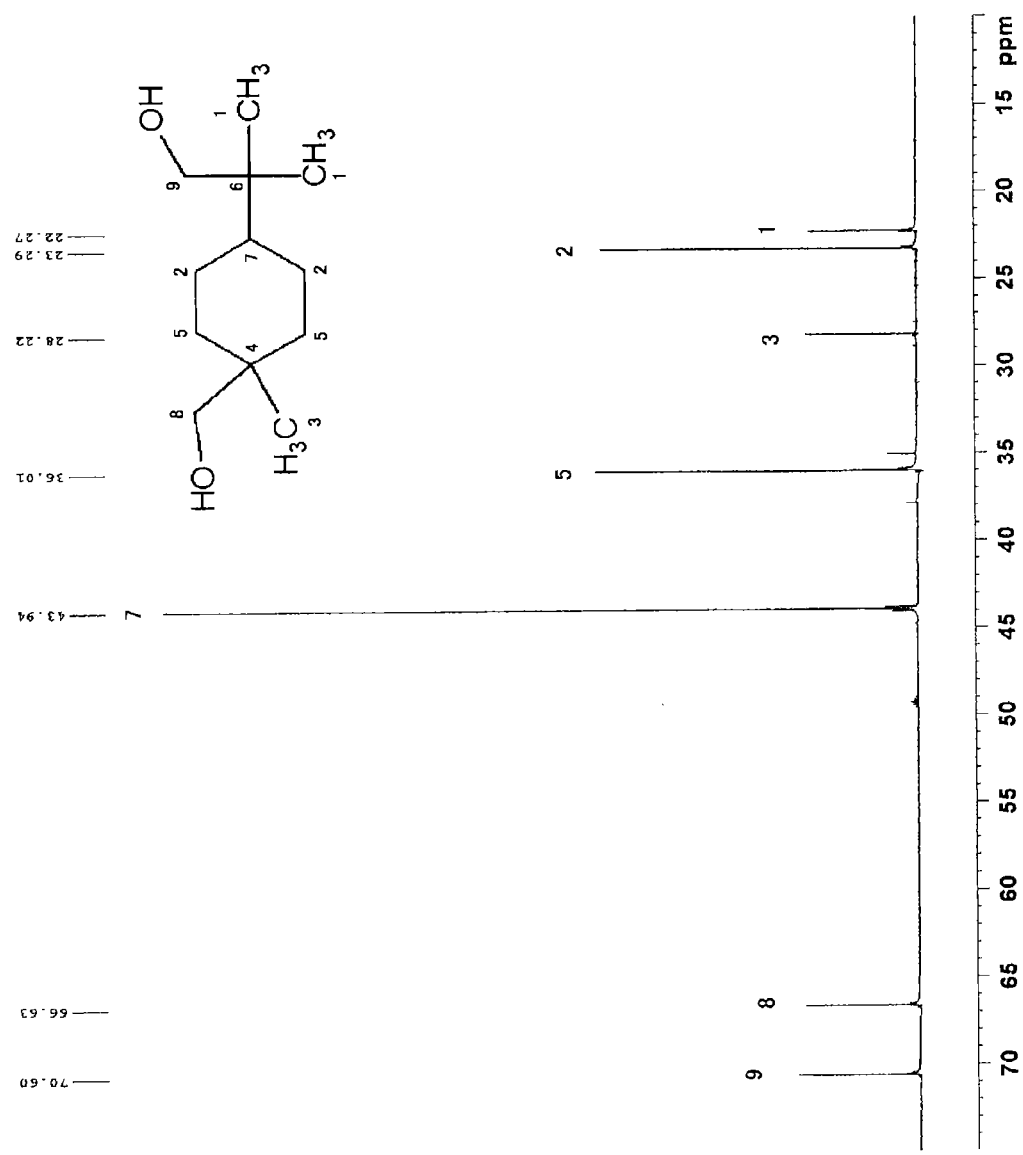
FIG. 2 is a chart showing DEPT 90°-NMR measurement results of a product obtained in Example 1.
Figure 3:
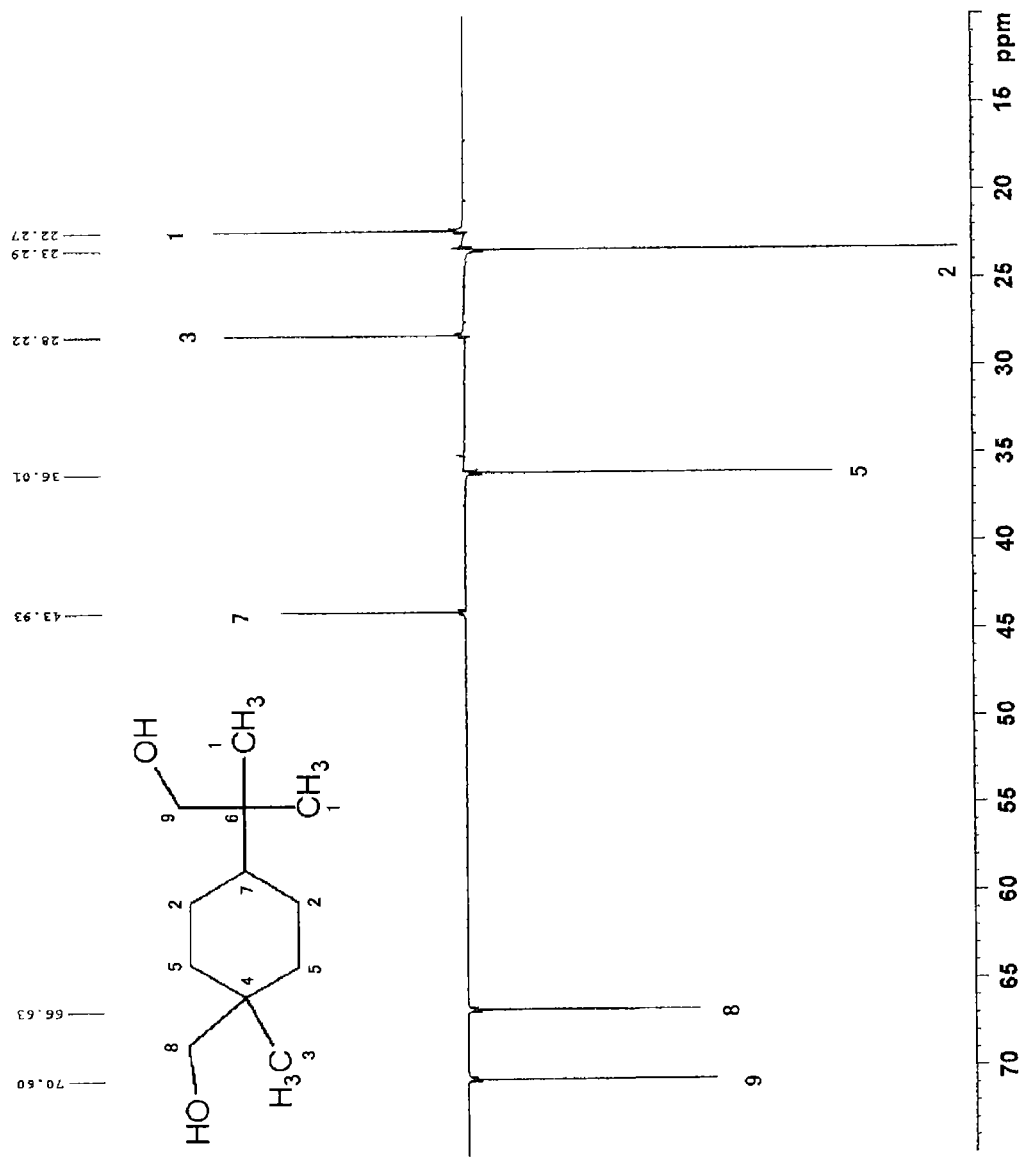
FIG. 3 is a chart showing DEPT 135°-NMR measurement results of a product obtained in Example 1.
Figure 4:
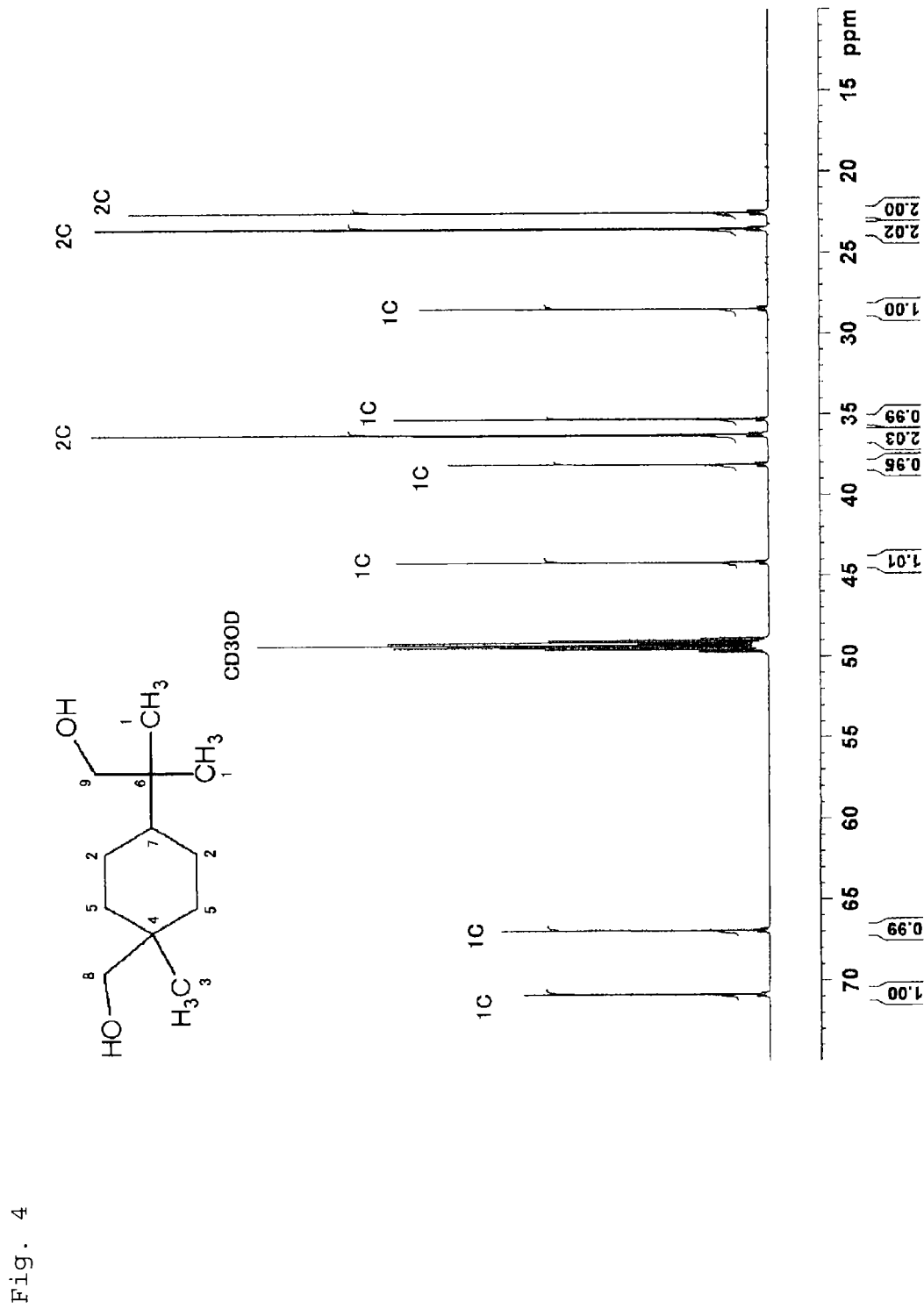
FIG. 4 is a chart showing Carbon i.g.-NMR measurement results of a product obtained in Example 1.
Figure 5:
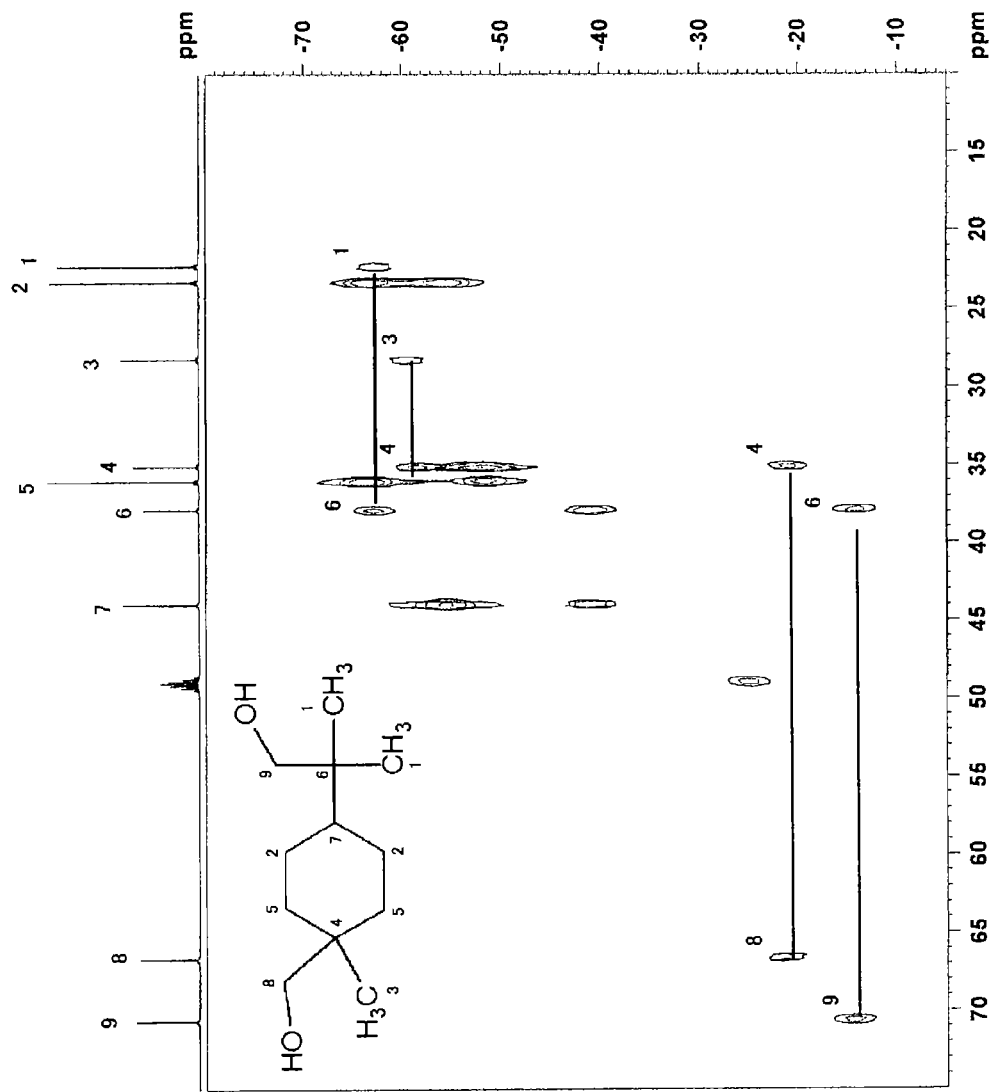
FIG. 5 is a chart showing INADEQUATE-NMR measurement results of a product obtained in Example 1.
Figure 6:
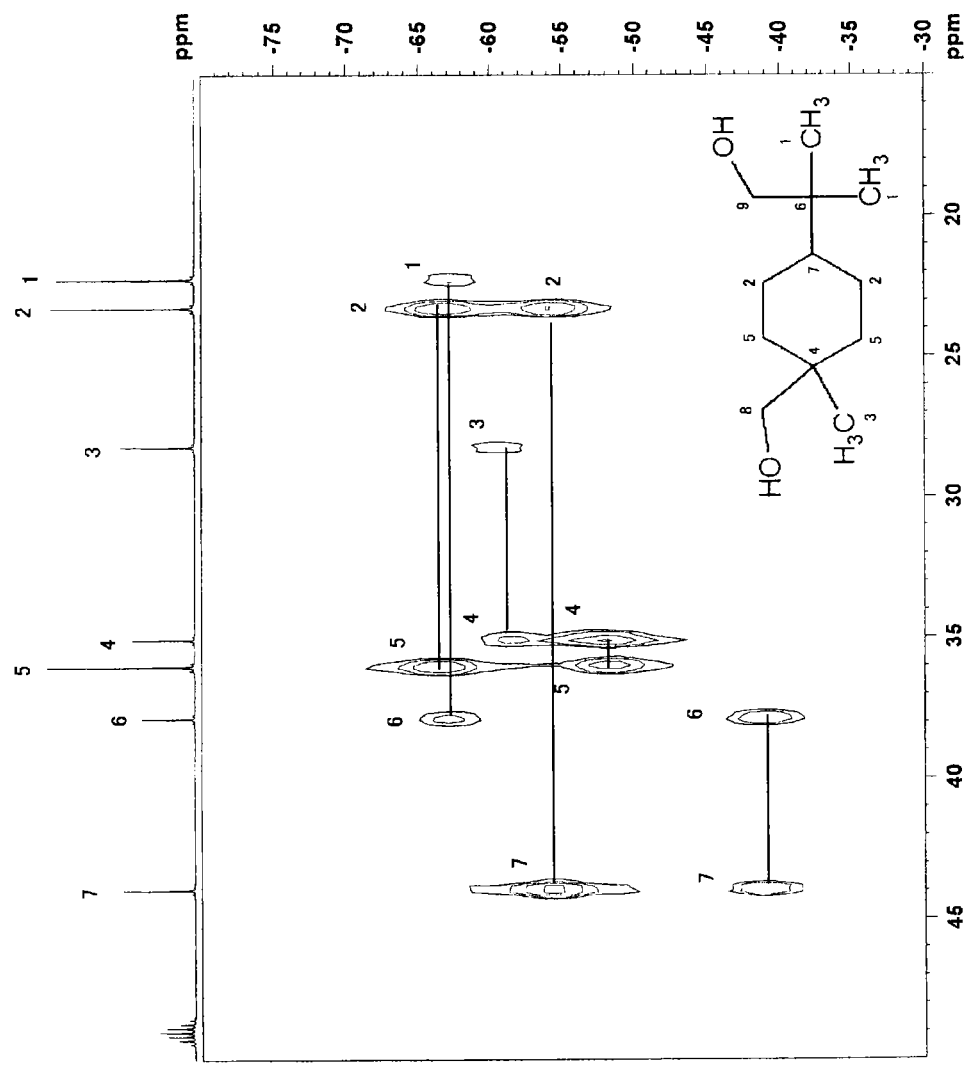
FIG. 6 is an enlarged chart showing measurement results in a portion from 15 to 50 ppm in FIG. 5.

FIG. 1 is a chart showing DEPT 45°-NMR measurement results. From FIG. 1, it was found that the fourth and sixth peaks for quaternary carbon atoms were missing. FIG. 2 is a chart showing DEPT 90°-NMR measurement results. From FIG. 2, it was found that the seventh peak for a tertiary carbon atom was strongly detected. FIG. 3 is a chart showing DEPT 135°-NMR measurement results. It was found that the second, fifth, eighth, and ninth peaks for secondary carbon atoms were detected in the downward direction. FIG. 4 is a chart showing Carbon i.g.-NMR measurement results. From FIG. 4, the number of carbon was confirmed. FIG. 5 and FIG. 6 are charts showing INADEQUATE-NMR measurement results (FIG. 6 is an enlarged chart showing measurement results in a portion for 15 to 50 ppm in FIG. 5.). From FIG. 5 and FIG. 6, the correlations of direct bonding between carbons were elucidated.

Based on comprehensive determination from the measurement results, the main component of the product obtained in Example 1 was identified to be 2-(4-(hydroxymethyl)-4-methylcyclohexyl)-2-methylpropan-1-ol.

INDUSTRIAL APPLICABILITY

The new alicyclic diol compound obtained in the present invention is useful as various industrial chemical raw materials and raw materials for manufacturing functional optical materials and functional electronic materials.

The invention claimed is:

1. An alicyclic diol compound of formula (1):

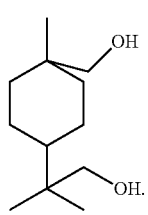

(1)

2. A method of manufacturing an alicyclic diol compound comprising:
reacting 4-isopropenyl-1-methyl-1-cyclohexene of formula (4) with carbon monoxide in the presence of hydrogen fluoride so as to produce an alicyclic dicarboxylic acid fluoride of formula (3);

reacting the produced alicyclic dicarboxylic acid fluoride of formula (3) with alcohol so as to produce an alicyclic dicarboxylic acid ester compound of formula (2); and reducing the produced alicyclic dicarboxylic acid ester compound of formula (2) so as to produce an alicyclic diol compound of formula (1):

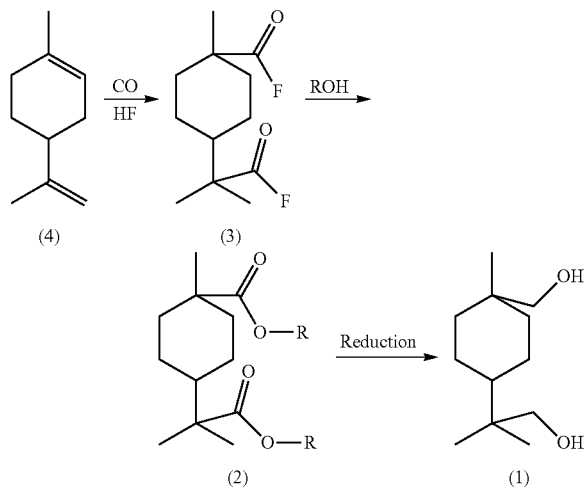

wherein R each independently represent an alkyl group having 1 to 4 carbon atoms.

3. The method of claim 2, wherein said reacting 4-isopropenyl-1-methyl-1-cyclohexene of formula (4) with carbon monoxide in the presence of hydrogen fluoride so as to produce an alicyclic dicarboxylic acid fluoride of formula (3) is under pressure of carbon monoxide.

4. The method of claim 3, wherein said reacting 4-isopropenyl-1-methyl-1-cyclohexene of formula (4) with carbon monoxide in the presence of hydrogen fluoride so as to produce an alicyclic dicarboxylic acid fluoride of formula (3) further comprises an inert gas.

5. The method of claim 4, wherein said inert gas is nitrogen or methane.

6. The method of claim 3, wherein said carbon monoxide is present at a carbon monoxide partial pressure in the range of 0.5 to 5 MPa.

7. The method of claim 2, wherein said hydrogen fluoride is substantially anhydrous.

8. The method of claim 2, wherein said hydrogen fluoride is present in an amount ranging from 4 to 30 times by mole per mole of 4-isopropenyl-1-methyl-1-cyclohexene.

9. The method of claim 2, wherein said reacting 4-isopropenyl-1-methyl-1-cyclohexene of formula (4) with carbon monoxide in the presence of hydrogen fluoride so as to produce an alicyclic dicarboxylic acid fluoride of formula (3) is at a temperature ranging from −50° C. to 30° C.

10. The method of claim 2, wherein said reacting 4-isopropenyl-1-methyl-1-cyclohexene of formula (4) with carbon monoxide in the presence of hydrogen fluoride so as to produce an alicyclic dicarboxylic acid fluoride of formula (3) is at a pressure ranging from 0.6 to 5.0 MPa.

11. The method of claim 2, wherein hydrogen fluoride is removed by distillation after said reacting 4-isopropenyl-1-methyl-1-cyclohexene of formula (4) with carbon monoxide in the presence of hydrogen fluoride so as to produce an alicyclic dicarboxylic acid fluoride of formula (3) and before said reacting the produced alicyclic dicarboxylic acid fluoride of formula (3) with alcohol so as to produce an alicyclic dicarboxylic acid ester compound of formula (2).

12. The method of claim 2, wherein said alcohol is at least one selected from the group consisting of methanol, ethanol, n-propanol, isopropanol, n-butyl alcohol, isobutyl alcohol, and tert-butyl alcohol.

13. The method of claim 2, wherein said alcohol is added in an amount ranging from 1.0 to 2.5 times by mole per mole of 4-isopropenyl-1-methyl-1-cyclohexene.

14. The method of claim 2, wherein said reacting the produced alicyclic dicarboxylic acid fluoride of formula (3) with alcohol so as to produce an alicyclic dicarboxylic acid ester compound of formula (2) is at a temperature ranging from −40° C. to 20° C.

15. The method of claim 2, wherein reducing the produced alicyclic dicarboxylic acid ester compound of formula (2) so as to produce an alicyclic diol compound of formula (1) is selected from the group consisting of a hydride reduction, reduction using a metal and a metal salt, and reduction by catalytic hydrogenation.

16. The method of claim 2, wherein reducing the produced alicyclic dicarboxylic acid ester compound of formula (2) so as to produce an alicyclic diol compound of formula (1) is reduction by catalytic hydrogenation.

17. The method of claim 16, wherein said catalytic hydrogenation comprises 1 to 100 parts by mass of a catalytic hydrogenation catalyst relative to 100 parts by mass of the alicyclic dicarboxylic acid ester compound.

18. The method of claim 2, wherein reducing the produced alicyclic dicarboxylic acid ester compound of formula (2) so as to produce an alicyclic diol compound of formula (1) is in the absence of a solvent.

19. The method of claim 2, wherein reducing the produced alicyclic dicarboxylic acid ester compound of formula (2) so as to produce an alicyclic diol compound of formula (1) is in the presence of at least one solvent selected from the group consisting of water, an organic acid, an aromatic compound, a hydrocarbon, an alcohol, and an ether.

20. The method of claim 19, wherein said at least one solvent is present in an amount of up to 30 times by mass based on the amount of alicyclic dicarboxylic acid ester compound of formula (2) produced in the esterification step.

21. The method of claim 2, wherein reducing the produced alicyclic dicarboxylic acid ester compound of formula (2) so as to produce an alicyclic diol compound of formula (1) is at a hydrogen pressure ranging from 1 to 30 MPa.

22. The method of claim 2, wherein reducing the produced alicyclic dicarboxylic acid ester compound of formula (2) so as to produce an alicyclic diol compound of formula (1) is at a temperature ranging from 100° C. to 300° C.

23. The method of claim 2, wherein reducing the produced alicyclic dicarboxylic acid ester compound of formula (2) so as to produce an alicyclic diol compound of formula (1) is at a pressure ranging from 1.5 to 30 MPa.

* * * * *